United States Patent [19]

Cramer et al.

[11] Patent Number: 5,283,808
[45] Date of Patent: Feb. 1, 1994

[54] X-RAY DEVICE HAVING A CO-AXIAL LASER AIMING SYSTEM IN AN OPPOSED CONFIGURATION

[75] Inventors: Steven L. Cramer, Sandy; Li Yuan, Salt Lake City, both of Utah

[73] Assignee: Diasonics, Inc., Milpitas, Calif.

[21] Appl. No.: 908,320

[22] Filed: Jul. 1, 1992

[51] Int. Cl.$^5$ .............................................. A61B 6/08
[52] U.S. Cl. ..................................... 378/206; 378/205
[58] Field of Search .............................. 378/205, 206

[56] References Cited

U.S. PATENT DOCUMENTS

| 4,223,227 | 9/1980 | Horwitz . | |
|---|---|---|---|
| 4,618,980 | 10/1986 | Lescrenier et al. | 378/206 |
| 5,031,203 | 7/1991 | Trecha | 378/206 |

OTHER PUBLICATIONS

Advertisement for "Focal Distance Indicator" from Gammex, Inc.

*Primary Examiner*—Craig E. Church
*Attorney, Agent, or Firm*—Blakely, Sokoloff, Taylor & Zafman

[57] ABSTRACT

An improved x-ray laser aiming system providing coaxial laser aiming in a configuration opposed to the x-ray emitter is disclosed. The present invention comprises two basic components: 1) a laser sight coupled to an x-ray emitter, and 2) a laser housing coupled to an x-ray collector. The laser sight provides a means for aligning the x-ray emitter with a laser beam during surgical or diagnostic procedures. The laser housing is removably coupled to the image intensifier or x-ray collector. The laser housing contains a point laser source and a fixed reflective surface or mirror for directing a laser beam coaxially with the center ray of the x-rays emitted by the x-ray emitter, but in the opposite direction. The laser source is, therefore, in a configuration opposed or opposite to the x-ray emitter. The laser aiming system of the present invention may be used to provide a reference point during orthopedic alignment procedures such as pinning and for vascular procedures such as balloon angioplasty, and correction of conditions involving embolisms, aneurysms, or arterial venous malformations (AVM's).

14 Claims, 4 Drawing Sheets

FIG_1
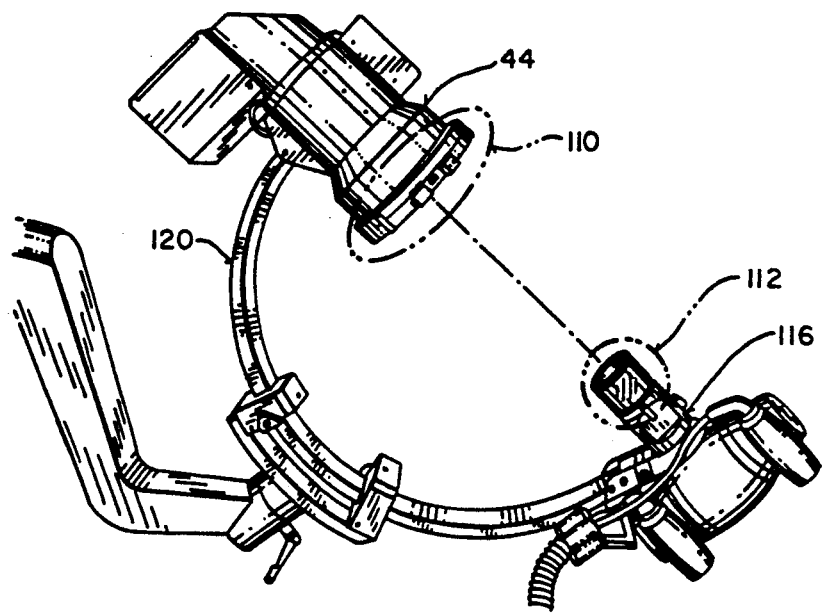
FIG_2
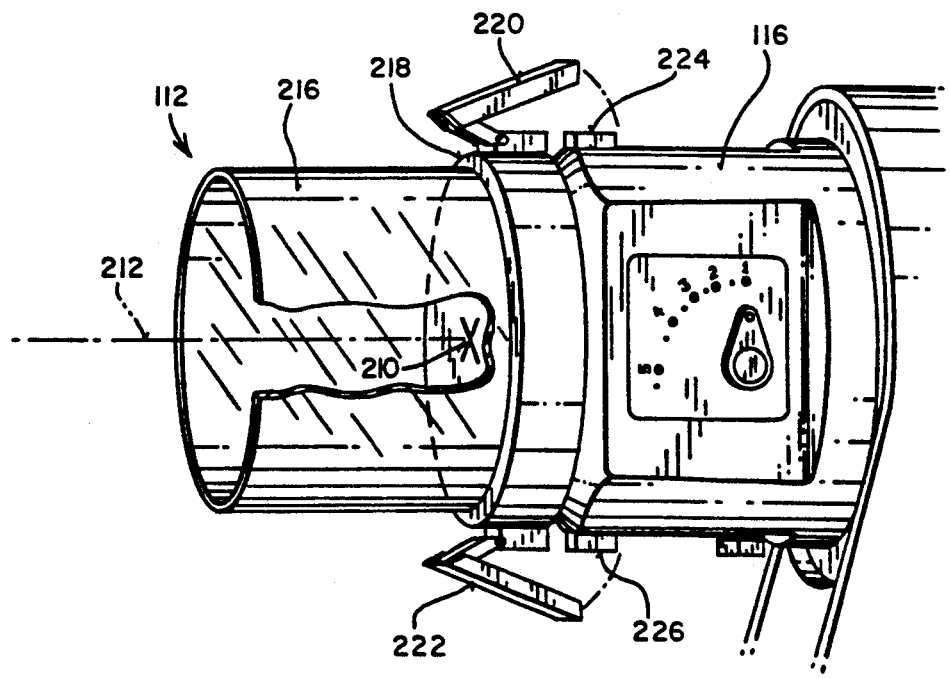

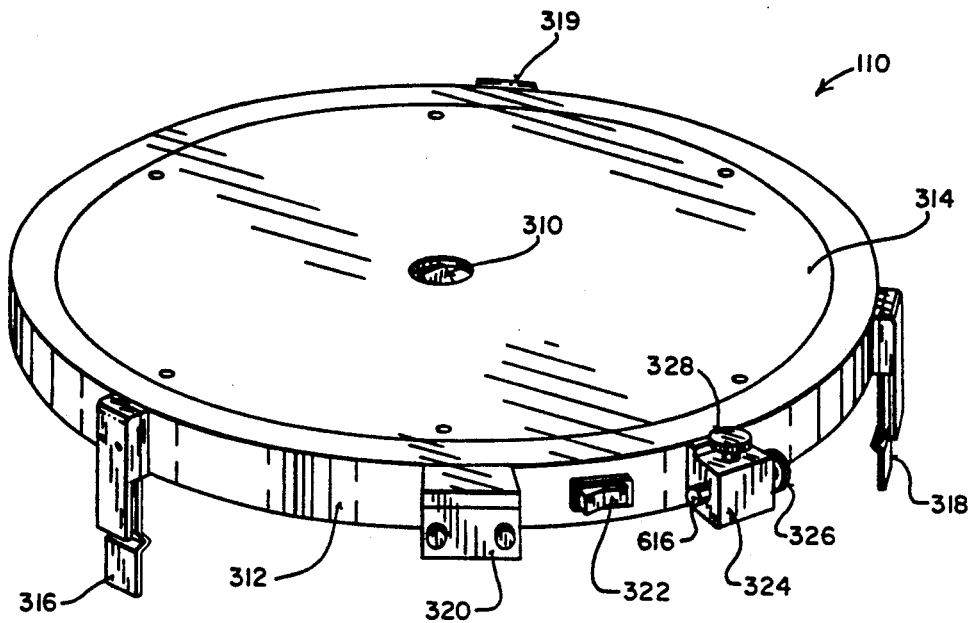
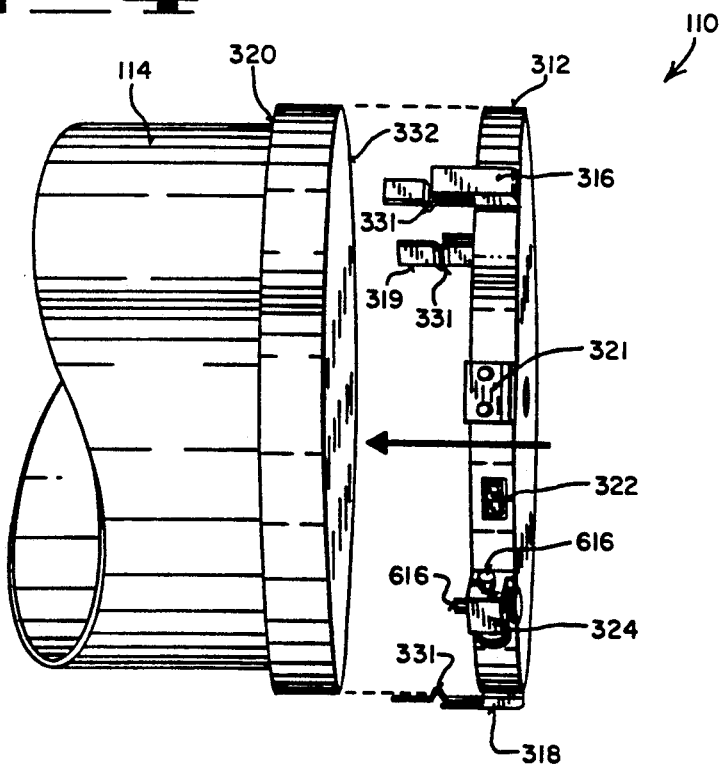

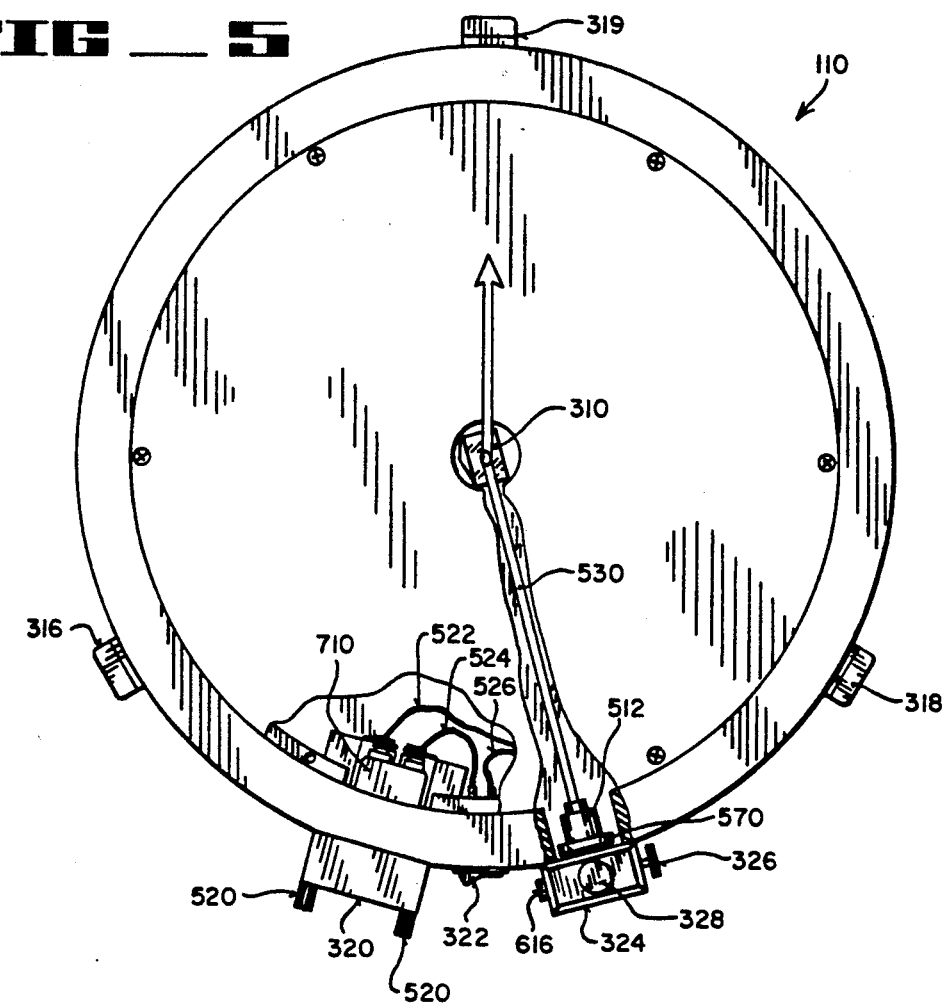
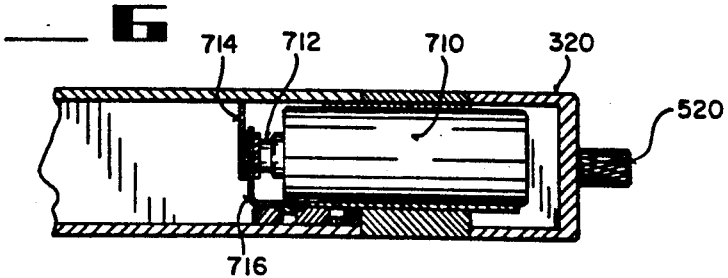

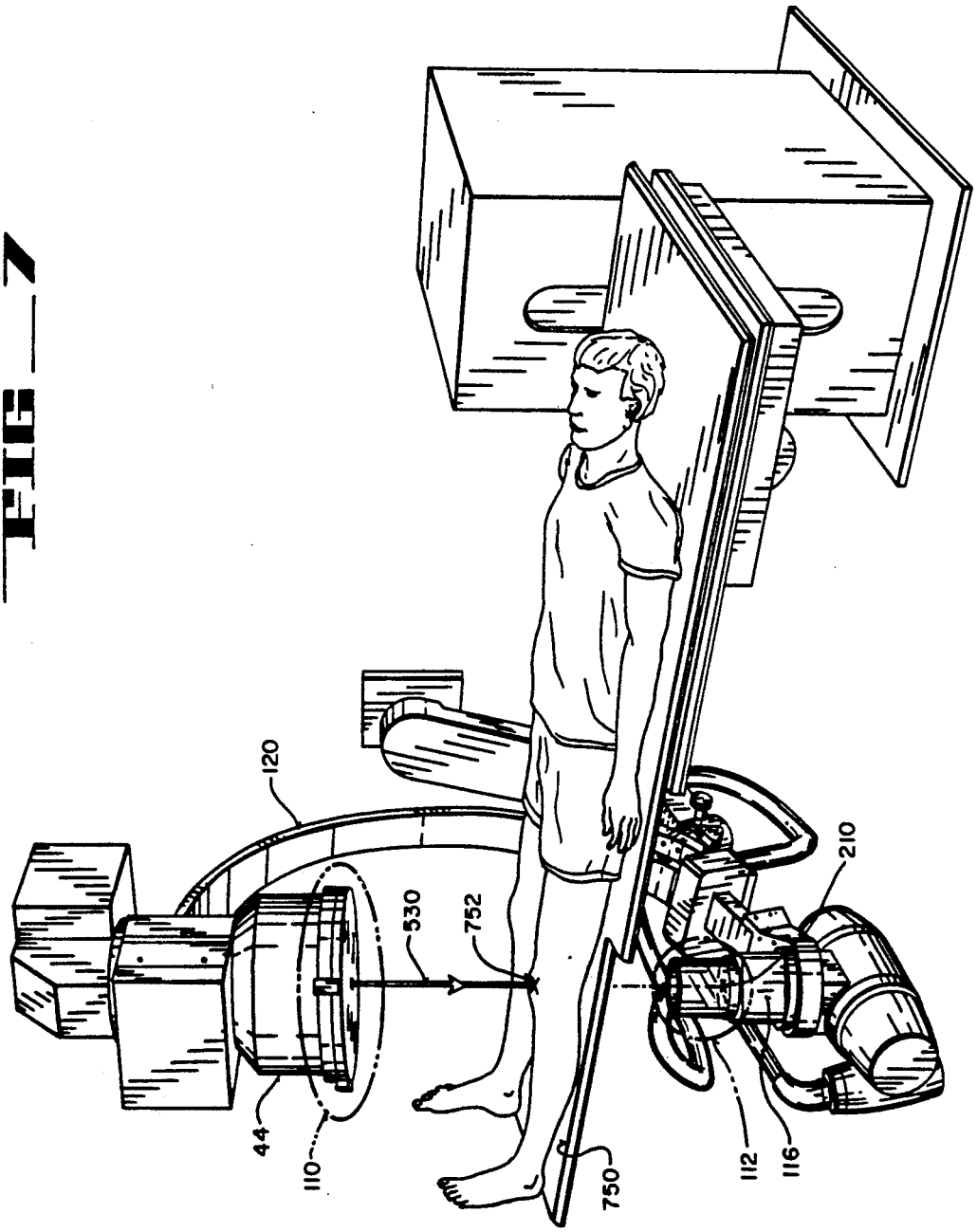

X-RAY DEVICE HAVING A CO-AXIAL LASER AIMING SYSTEM IN AN OPPOSED CONFIGURATION

BACKGROUND OF THE INVENTION

1. Field of the Invention

The present invention pertains to the field of x-ray machine positioning systems. Specifically, the present invention relates to the use of a laser aiming system with a C-arm x-ray machine.

2. Prior Art

Laser light beams have been used in prior art systems for positioning various types of equipment. One such positioning system is disclosed in U.S. Pat. No. 5,031,203, titled *Co-axial Laser Targeting Device For Use With X-ray Equipment And Surgical Drill Equipment During Surgical Procedures*, invented by Randal R. Trecha (hereinafter denoted the '203 Patent). The '203 Patent discloses an apparatus including a laser light emitting means (laser source) disposed on an x-ray gun portion for emitting a beam of visible laser light. This apparatus includes a target grid means disposed on the x-ray collector portion for targeting the visible laser light in co-axial relationship with the longitudinal axis of the x-ray radiation between the gun portion and the collector portion of the x-ray equipment. The apparatus described in the '203 Patent further includes a radiolucent plastic mirror assembly mounted on the laser emitter. The central ray of the x-ray shares the path of the laser as it is reflected off the mirror, so that the x-ray and the laser are co-axial with one another. The apparatus described in the '203 Patent is useful for locating interlocking screw holes in intramedullary rods, placement of pedicle screws in spinal surgery, placement of wires for percutaneous and open fixation, accurate positioning of the image intensifier without exposure to radiation, and accurate percutaneous pin placement of an external fixation in pelvic fractures.

The apparatus described in the '203 Patent has several disadvantages. First, the configuration described in the '203 Patent requires that the x-ray emitter and the laser source be positioned above the level of a table upon which a patient or subject is situated. If this were not the case, the table would shield the laser beam and render the targeting apparatus unusable. In actual practice, x-ray emitters are often positioned below the level upon which patients or subjects are situated. In fact, C-arm mounting supports are well known and used in prior art x-ray systems for the purpose of positioning an x-ray emitter in any arbitrary position about a subject under examination or surgical operation including below table level. The configuration of the apparatus described in the '203 Patent substantially limits the utility of the C-arm support structure.

A second disadvantage of the apparatus described in the '203 Patent again pertains to the fact that the laser source is disposed on the x-ray emitter or x-ray gun portion of the x-ray device. In this configuration, the x-ray emitter must always be positioned above the level of the table upon which a patient or subject is situated. When the x-ray emitter is positioned in this manner, the operating room staff is fully exposed to scatter radiation emitted from the primary x-ray beam and to non-attenuated x-ray beam radiation from the x-ray emitter. When the x-ray emitter is positioned below the level of the table, the patient and the patient table absorb much of the scatter radiation, and attenuate the x-ray beam. This reduces radiation to the operating room staff, particularly radiation to the staff's hands, faces, and eyes. Thus, although the apparatus described in the '203 Patent may provide a co-axial laser targeting device, significant problems in the practical application of the device limit the utility of the apparatus.

Other laser targeting systems for x-ray machines are available from Gammex, Inc. of Milwaukee, Wis. The Gammex laser systems use two laser sources disposed on the x-ray emitter that together form a visible crosshair of light that defines the center ray of the x-ray emitter. The Gammex system is similar to the apparatus described in the '203 Patent in that the laser source is disposed on the x-ray emitter; however, the Gammex laser system does not emit a point laser co-axial with the center beam of the x-ray emitter. Rather, the Gammex laser targeting system comprises two laser sources. One laser source emits a fan laser beam in a generally horizontal direction, while the other laser emitter emits a fan beam generally oriented in a vertical direction. The two fan laser beams are calibrated to cross at a point corresponding to a position on the center beam of the x-ray emitter. Because the Gammex system comprises two laser sources, the laser targeting system is more difficult to calibrate with the x-ray emitter.

U.S. Pat. No. 4,442,533 discloses an indicator for visibly defining the image plane located at the moveable fulcrum of a tomography x-ray machine. The indicator includes a laser beam light source mounted for vertical movement along a rack and pinion assembly. This indicator does not provide an indication of the longitudinal axis of the central x-ray beam as would be required when making transverse bores in a patient's bone in register with the bores of an osteosynthesis aid in the bone.

U.S. Pat. No. 4,426,726 discloses an apparatus and method for aligning the center of an x-ray beam with both a reference point on a patient and the center of the x-ray film holder. A visible light source is disposed on an x-ray emitter in a manner similar to the '203 Patent. The visible light source emits two fan beams which provide two fan beam planes. The fan beam planes perpendicularly bisect the x-ray beam and each other to form a line of intersection corresponding to the center of the x-ray beam. In a manner similar to the Gammex laser devices, the two visible light sources emit fan beams that may be calibrated to correspond to the center beam of the x-ray emitter. Again, however, the visible light source is not co-axial with the center beam of the x-ray emitter. Moreover, because the device has two visible light sources, the apparatus is more difficult to calibrate.

The light beam producing device described in U.S. Pat. No. 4,337,502 also describes an apparatus for producing vertical and horizontal planes of visible light. The intersection of the light planes with the body of the subject under examination forms luminous lines that may be used to properly orient the patient with respect to the light lines.

Laser light beams have also been used to calibrate tomography machines using phantoms as disclosed in U.S. Pat. No. 4,296,329, and for calibrating linear accelerators, or a cobalt-60 teletherapy machine as is disclosed in U.S. Pat. Nos. 4,123,660 and 4,223,227.

U.S. Pat. No. 4,625,718 discloses an aiming apparatus for making transverse bores in a patient's bone in register with the holes or bores of an osteosynthesis aid in the bone. This apparatus includes an aiming member adapted to be brought into the beam path of an x-ray device. This apparatus is difficult to use and typically not as accurate as a laser targeting device.

Thus, a better means is needed for aiming an x-ray emitter with a laser aiming device.

SUMMARY OF THE INVENTION

The present invention is an improved x-ray laser aiming system providing coaxial laser aiming in a configuration opposed to the x-ray emitter. The present invention comprises tow basic components: 1) a laser sight coupled to an x-ray emitter, and 2) a laser housing coupled to an x-ray collector. The laser sight provides a means for aligning the x-ray emitter with a laser beam during surgical or diagnostic procedures. The laser housing is removably coupled to the image intensifier or x-ray collector. The laser housing contains a point laser source and a fixed reflective surface or mirror for directing a laser beam coaxially with the center ray of the x-rays emitted by the x-ray emitter, but in the opposite direction. The laser source is, therefore, in a configuration opposed or opposite to the x-ray emitter.

The opposed configuration of the present invention improves versatility by facilitating use of the system with a C-arm structure. The opposed configuration in combination with the C-arm structure allows a greater useful range of movement and positioning of the x-ray emitter than possible with prior art systems. The extended useful range of movement and positioning of the x-ray emitter includes the ability to position the x-ray emitter underneath a patient or below the level of a surface upon which a subject is situated. As positioned in this manner, the present invention improves safety by reducing the potential for x-ray exposure to the attending physicians and surgical personnel when the x-ray system is in operation. When the x-ray emitter is positioned below the level of the table, scatter radiation that may otherwise contact attending personnel is blocked or attenuated by either the patient or the surface upon which a subject is situated.

The laser aiming system of the present invention may be used to provide a reference point during orthopedic alignment procedures such as pinning and for vascular procedures such as balloon angioplasty, and correction of conditions involving embolisms, aneurysms, or arterial venous malformations (AVM's).

BRIEF DESCRIPTION OF THE DRAWINGS

FIG. 1 illustrates an x-ray machine on a C-arm with the laser aiming system of the present invention attached.

FIG. 2 illustrates the laser sight of the present invention as disposed on the x-ray emitter.

FIG. 3 illustrates the laser housing of the present invention.

FIG. 4 illustrates the laser housing of the present invention as disposed on the image intensifier or collector portion of the x-ray machine.

FIG. 5 illustrates a cutaway view of the laser housing showing a laser source, a reflector, a power source, and a power switch.

FIG. 6 illustrates a battery housing as disposed in the laser housing.

FIG. 7 illustrates a typical orientation of the present invention as used in practice.

DETAILED DESCRIPTION OF THE PREFERRED EMBODIMENT

The present invention is an improved x-ray laser aiming system providing coaxial laser aiming in a configuration opposed to the x-ray emitter.

In the following description, numerous specific details are set forth in order to provide a thorough understanding of the invention, however, it will be apparent to one of ordinary skill in the art that these specific details need not be used to practice the present invention. In other circumstances, well-known structures, x-ray machine details, and other well-known aspects have not been shown in detail in order not to unnecessarily obscure the present invention.

Referring to FIG. 1, an x-ray machine suitable for use with the present invention is illustrated. The x-ray machine comprises an x-ray emitter 116 and an x-ray collector or image intensifier 44 both positioned on a C-arm support structure 120. The x-ray machine illustrated in FIG. 1 operates as well-known in the art, to emit x-ray radiation from source 116. This x-ray radiation is received by a collector 44 also called an image intensifier. A subject under examination or surgery, is positioned between x-ray emitter 116 and collector 44. In this manner, x-ray images of the subject may be captured by collector 44 and processed for visual display. It will be apparent to those skilled in the art that the x-ray emitter 116 is always positioned opposite or opposed to the collector 44. C-arm 120 is conveniently used for positioning the x-ray emitter 116 opposite the collector 44; however, C-arm 120 may equivalently be replaced by a stationary support structure in an alternative x-ray machine implementation.

The present invention is a laser aiming system for an x-ray machine such as the one illustrated in FIG. 1. The present invention comprises two basic components: 1) a laser sight 112 coupled to x-ray emitter 116, and 2) a laser housing 110 coupled to the collector 44. Laser sight 112 provides a means for aligning the x-ray emitter 116 with a laser beam during surgical or diagnostic procedures. Laser sight 112 is described in more detail in connection with FIG. 2. The second component of the present invention is laser housing 110. The laser housing 110 is removably coupled to the image intensifier or x-ray collector 44. Laser housing 110 contains a laser source and a fixed reflective surface or mirror for directing a laser beam coaxially with the center ray of the x-rays emitted by x-ray emitter 116, but in the opposite direction. The laser source is, therefore, in a configuration opposed or opposite to the x-ray emitter. Laser housing 110 is described in more detail in connection with FIGS. 3–6.

Referring now to FIG. 2, the laser sight 112 of the present invention is illustrated. Laser sight 112 is comprised of a cylindrical body 216 and a cap 218. In the preferred embodiment, laser sight body 216 is fabricated from a translucent plastic material to facilitate viewing the laser beam 212 as it strikes the surface of cap 218 at centerpoint 210. Laser sight cap 218 is a cylindrical part fabricated of a diameter matched to the dimension of x-ray emitter 116. Cap 218 fits over an end of x-ray emitter 116 and snaps into place with latches 220 and 222. Latches 220 and 222 fit over the top of tab stops 224 and 226 and lock into place in a conventional manner. Once latches 220 and 222 are locked into place, laser sight 112 is removably attached to x-ray emitter 116. Laser sight cap 218 also includes a radio-opaque reference point or mark 210 at the center of cap 218. Reference point 210 appears in the center of a flouro-image when x-ray emitter 116 is operating. Reference point 210 is used to align laser beam 212 with the center ray of the x-rays emitted by emitter 116. Laser sight 112 may be removed from x-ray emitter 116 by releasing latches 220 and 222 by pulling one side of latches 220 and 222 away from cap 218 in a conventional use of latches such as latches 220 and 222.

Referring now to FIG. 3, the laser housing 110 of the present invention is illustrated. Laser housing 110 is comprised of a perimeter ring 312 to which an upper circular plate 314 and a lower circular plate (not shown) are permanently attached using a conventional screw or bolt attaching method. As fabricated in this matter, a cylindrical cavity within laser housing 110 is formed. This cavity is shown in cross-section in FIG. 6.

In the preferred embodiment, perimeter ring 312 is fabricated of a light weight metal such as aluminum. It will be apparent to those skilled in the art that laser housing 110 may be fabricated of most any material including metal or plastic which is rigid and strong enough to span the surface of image intensifier 114, yet does not interfere with the operation of the x-ray machine.

Upper surface plate 314 of laser housing 110 includes a small hole at the center in which an angled reflective mirror (i.e. laser light reflector) 310 is permanently affixed within the cavity of laser housing 110. The mirror 310 is used to reflect a laser beam into coaxial alignment with the center ray of the x-rays emitted by x-ray emitter 116. The reflective surface of mirror 310 is, therefore, angled toward a laser source (laser source 512 is shown in FIG. 5) and the x-ray emitter 116. Mirror 310 is a plastic mirror in the preferred embodiment. In the preferred embodiment, mirror 310 is permanently affixed to laser housing 110 and does not provide a means for adjusting the direction of a laser beam striking the reflective surface. In the present invention, the direction of travel of the laser beam is adjusted by manipulating the laser source itself as will be described below.

Spring clips 316, 318, and 319 are adjustably attached to ring 312 at equidistant positions around the circumference. Spring clips 316, 318, and 319 provide a means for removably attaching housing 110 to image intensifier 114 as shown in FIG. 4 and described below.

Coupled to ring 312 of laser housing 110 are three additional components of the laser aiming system of the present invention. A laser source 512 is installed within a laser housing 324 as shown in FIGS. 3, 4, and 5. The laser source 512 used in the present invention is a conventional semiconductor type Class IIIa laser product with a peak power of 5 mw and a wavelength of 670 nm. A laser source such as the one used in the present invention is available from Applied Laser Systems Corporation of Oregon.

The second component coupled to ring 312 is a battery housing 320 within which a battery for powering the laser source is installed. The structure and operation of battery housing 320 is described in more detail in connection with FIGS. 5 and 6.

The third component of the present invention installed in ring 312 is switch 322. Switch 322 is a power on/off switch for energizing or de-energizing the laser light source. Switch 322 is described in more detail in connection with FIG. 5.

Referring now to FIG. 4, the installation of laser housing 110 onto image intensifier 114 is illustrated. Laser housing 110 includes springclips 316, 318, and 319. Springclips 316, 318, and 319 are adjustably attached to ring 312 of laser housing 110. The springclips 316, 318, and 319 are independent attachable components attached using screws in the preferred embodiment. Springclips 316, 318, and 319 are fabricated from conventional metallic material of an elastic nature. Each springclip is crimped to produce a protruding ridge 331 on the inner side (nearest the center of laser housing 110) of the springclip. As the laser housing 110 is moved into contact with image intensifier 114, the springclips 316, 318, and 319 are deflected outwardly until the protruding ridge 331 falls over the edge 320 of image intensifier 114. As springclips 316, 318, and 319 snap over the edge 320, the laser housing 110 is removably attached to image intensifier 114. Laser housing 110 may be held in place a predetermined distance above the circular face 332 of image intensifier 114 by springclips 316, 318, and 319. Laser housing 110 is removed from image intensifier 114 by simply pulling laser housing 110 away from image intensifier 114 thereby deflecting springclips 316, 318, and 319 away from the edge 320 and releasing laser housing 110 therefrom. By easily snapping laser housing 110 on and off, the clinical utility of the laser aiming system of the present invention is improved. It should be noted that no electrical or mechanical linkage other than springclips 316, 318, or 319 are required between laser housing 110 and image intensifier 114. This is due in part to the fact that the power source within battery housing 321 for powering the laser source 512 is coupled to the laser housing 110 itself.

Referring now to FIG. 5, a cutaway view of laser housing 110 is illustrated. Laser housing 110 includes battery housing 320 in which a battery 710 is installed. Battery housing 320 is secured to laser review assembly housing 110 using locking screws 520.

Referring now to FIG. 6, a side view of battery housing 320 is illustrated. In the preferred embodiment, battery 710 is a nine volt batter suitable for powering the laser source 512. Batteries of this type are well known and commonly available in the prior art. When installed within battery housing 320, battery 710 makes electrical contact with contacts 714 and 716. Referring again to FIG. 5, wires 522 and 524 are electrically connected to contacts 714 and 716. Wire 524 is routed through switch 322, and both wires 522 and 526 are electrically connected to laser source 512. In the configuration as shown in FIGS. 5 and 6, power for laser source 512 is provided by battery 710 and can be turned on or off using switch 322. The laser light source 512 and power for same is therefore wholly contained within laser housing 110. No external connections are required.

The laser source 512 used in the preferred embodiment of the present invention is a semiconductor laser device with a power rating of approximately 3–5 milliwatts. Laser 512 is adjustably mounted by a universal joint 570 within laser housing 324. Use of a universal joint for adjusting a laser is well known in the art. Two adjustment screws 326 and 328 are provided in laser housing 324 for the purpose of adjusting the direction of travel of laser beam 530. In two orthogonal directions, adjustment screws 326 and 328 are used to apply pressure to one end of laser 512. Compression springs 616 provide a compensating force in a direction opposite that of each adjustment screw 326 and 328. Compression springs 616 provide a force against one end of laser 512 in a direction opposite that of each adjustment screw 326 and 328. In this manner, the laser 512 can be deflected in two dimensions to adjustably calibrate the direction of travel of laser beam 530 in two dimensions. As laser beam 530 is emitted from laser 512, the laser beam 530 strikes the reflective surface of mirror 310 and is deflected towards x-ray emitter 116. Because the present invention uses an adjustably mounted laser source 512, reflective mirror 310 is permanently fixed in place in the center of laser device assembly housing 110. Mirror 310 is not adjustably mounted. Mirror 310 may be permanently mounted using a conventional glue or other bonding agent. Because mirror 310 does not need to be adjustably mounted, no calibration linkage or other mechanical or electrical apparatus needs to be connected to mirror 310. This is advantageous because any such linkage or calibration apparatus located near mirror 310 would clutter the x-ray image produced when the laser housing 110 was used in actual practice. It is advantageous, therefore, to reduce, as much as possible, the number and size of the components located at the center of laser housing 110. The present invention accomplishes this goal by requiring only the small mirror 310 permanently and fixedly mounted in the center of laser housing 110 and by locating all the laser adjustment apparatus at the outer perimeter of laser housing 110.

Referring now to FIG. 7, the present invention is illustrated as used in a typical application. As described above, the laser housing 110 and the laser source 512 therein emits a point laser beam 530 coaxial with but in a direction opposite than that of the center ray of the x-rays emitted by x-ray emitter 116. The laser source and the x-ray emitter are thus in an opposed configuration in the present invention. The opposed configuration of the present invention improves versatility by facilitating use of the system with a C-arm structure 120. The opposed configuration in combination with the C-arm structure 120 allows a greater useful range of movement and positioning of the x-ray emitter 116 than possible with prior art systems. The extended useful range of movement and positioning of the x-ray emitter 116 includes the ability to position the x-ray emitter 116 underneath a patient or below the level of a surface 750 upon which a subject is situated as illustrated in FIG. 7. As positioned in this manner, the present invention improves safety by reducing the potential for x-ray exposure to the attending physicians and surgical personnel when the x-ray system is in operation. When x-ray emitter 116 is positioned below the level of table 750, scatter radiation that may otherwise contact attending personnel is blocked or attenuated by either the patient or the surface 750 upon which a subject is situated.

The laser aiming system of the present invention as described above may be used to provide a reference point during orthopedic alignment procedures such as pinning. An example of such a procedure is illustrated in FIG. 7. Such a procedure is performed using the present invention by first attaching laser sight 112 to x-ray emitter 116 and attaching laser housing 110 to image intensifier 44 as shown in FIG. 7. As described above, laser sight 112 includes a radio-opaque reference point 210. When the x-ray emitter 116 is in operation, reference point 210 is positioned at a point of interest on the patient's anatomy. This point of interest may be a location at which a screw or pin is to be inserted into or removed from the patient. Reference point 210 may be positioned in relation to a patient by adjusting C-arm 120. Once reference point 210 is properly positioned, the laser source in laser housing 110 is energized using switch 322. Because the laser source in laser housing 110 is calibrated to emit laser beam 530 coaxial with the center ray of the x-rays emitted by x-ray emitter 116, laser beam 530 provides a reference point 752 on the patient's anatomy corresponding to the point aligned with reference point 210. Reference point 752 illuminated by laser beam 530 is then used by surgical personnel as an incision or drill point reference. With an accurate reference point, pinning or other similar operations can be performed using techniques well known in the art.

The present invention is also useful for applications other than orthopedic procedures, such as the one illustrated above. These other procedures include vascular procedures such as balloon angioplasty, and correction of conditions involving embolisms, aneurysms, or arterial venous malformations (AVM's). These vascular procedures involve the accurate placement of a catheter within the body. Accurate placement is facilitated by use of the external reference point provided by the laser aiming system of the present invention. Other applications of the present invention will become apparent to those skilled in the art.

Thus a laser aiming system for use with an x-ray machine is described.

Although the present invention is described herein with reference to a specific embodiment, many modifications and variations therein with readily occur to those skilled in the art. Accordingly, all such variations and modifications are included within the intended scope of the present invention as defined by the following claims.

What is claimed is:

1. A laser aiming system for use with an x-ray machine having an x-ray emitter for emitting x-rays and an x-ray collector for receiving said x-rays, said laser aiming system comprising:
    a) a laser housing removably coupled to said x-ray collector, said laser housing including:
        i) a laser light source adjustably coupled to an outer perimeter of said laser device assembly, said laser light source producing a visible point laser beam,
        ii) a power source coupled to said laser device assembly and said laser light source, and
        iii) a laser light reflector immovably coupled to the center of said laser housing for redirecting said laser beam into coaxial alignment with said x-rays emitted by said x-ray emitter; and
    b) a laser sight removably coupled to said x-ray emitter, said laser sight having a radio-opaque reference mark disposed at the center of said laser sight.

2. The laser aiming system as claimed in claim 1 wherein said laser housing further includes spring clips coupled thereto for removably coupling said laser housing to said x-ray collector.

3. The laser aiming system as claimed in claim 1 wherein said power source is a battery disposed within said laser device assembly.

4. The laser aiming system as claimed in claim 1 wherein said laser housing further includes a switch coupled to said laser housing and electrically coupled to said power source and said laser light source, said switch for selectively electrically connecting or disconnecting said laser light source with said power source.

5. The laser aiming system as claimed in claim 1 wherein said laser housing further includes orthogonal adjustment screws for adjusting the orientation of said laser light source and the direction of said laser beam emitted therefrom.

6. The laser aiming system as claimed in claim 1 wherein said laser light source is a semiconductor laser device.

7. The laser aiming system as claimed in claim 6 wherein said semiconductor laser device has a power rating of at least 3-5 milliwatts.

8. The laser aiming system as claimed in claim 1 wherein said power source is a nine volt battery.

9. The laser aiming system as claimed in claim 1 wherein said x-ray emitter is positioned below the level of a patient being radiated by said x-ray emitter.

10. The laser aiming system as claimed in claim 1 wherein said laser light reflector is a radio-lucent plastic mirror.

11. With a laser aiming system and an x-ray machine having an x-ray emitter for emitting x-rays and an x-ray collector for receiving said x-rays, said laser aiming system having a laser device assembly including an adjustably mounted laser light source emitting a visible point laser beam and a laser sight including radio-opaque reference mark disposed at the center of said laser sight, a process for positioning said x-ray machine comprising the steps of:
  a) removably attaching said laser housing to said x-ray collector and energizing said laser light source;
  b) removably attaching said laser sight to said x-ray emitter and energizing said x-ray emitter;
  c) moving said x-ray emitter until said radio-opaque reference mark is positioned at a desired point on a subject; and
  d) operating upon a point of said subject identified by a location illuminated by said laser beam.

12. The process as claimed in claim 11 wherein said x-ray emitter is positioned below the level of said subject and said x-ray collector is positioned above the level of said subject.

13. The process as claimed in claim 11 further including a step of adjusting the orientation of said laser light source by aligning said laser beam with said radio-opaque reference mark.

14. The process as claimed in claim 11 further including the steps of:
  a) removing said laser housing from said x-ray collector; and
  b) removing said laser sight from said x-ray emitter.

* * * * *